United States Patent
Borgschulte et al.

(10) Patent No.: US 10,085,818 B2
(45) Date of Patent: Oct. 2, 2018

(54) DENTAL HANDPIECE

(75) Inventors: Markus Borgschulte, Munich (DE); Lapo Vitali, Florence (IT)

(73) Assignee: DENTSPLY SIRONA Inc., York, PA (US)

(*) Notice: Subject to any disclaimer, the term of this patent is extended or adjusted under 35 U.S.C. 154(b) by 657 days.

(21) Appl. No.: 14/342,548

(22) PCT Filed: Sep. 5, 2012

(86) PCT No.: PCT/EP2012/003725
§ 371 (c)(1),
(2), (4) Date: May 22, 2014

(87) PCT Pub. No.: WO2013/034291
PCT Pub. Date: Mar. 14, 2013

(65) Prior Publication Data
US 2015/0342702 A1 Dec. 3, 2015

(30) Foreign Application Priority Data
Sep. 9, 2011 (EP) .................................... 11007352

(51) Int. Cl.
| | |
|---|---|
| *A61C 1/00* | (2006.01) |
| *A61C 1/14* | (2006.01) |
| *A61C 1/06* | (2006.01) |
| *A61C 5/40* | (2017.01) |
| *A61C 5/42* | (2017.01) |
| *A61C 5/44* | (2017.01) |
| *A61C 1/18* | (2006.01) |

(52) U.S. Cl.
CPC ............ *A61C 1/003* (2013.01); *A61C 1/0023* (2013.01); *A61C 1/06* (2013.01); *A61C 1/14* (2013.01); *A61C 5/40* (2017.02); *A61C 5/42* (2017.02); *A61C 5/44* (2017.02); *A61C 1/186* (2013.01)

(58) Field of Classification Search
CPC ........... A61C 5/02; A61C 5/023; A61C 5/025; A61C 1/003; A61C 1/0023; A61C 1/06; A61C 1/14; A61C 1/186
See application file for complete search history.

(56) References Cited

U.S. PATENT DOCUMENTS 5,902,105 A * 5/1999 Uejima .................. A61C 5/025
433/27
5,980,248 A * 11/1999 Kusakabe ............ A61C 1/0007
433/131

(Continued)

*Primary Examiner* — Heidi M Eide
(74) *Attorney, Agent, or Firm* — David A. Zdurne; Douglas J. Hura; Leana Levin

(57) ABSTRACT

Described herein is a dental handpiece for the endodontic treatment of a root canal, including a chuck for attaching and holding an endodontic file, an electric motor having a shaft for driving the endodontic file, and a control unit for controlling the motor, which receives a stream of input data. While monitoring the stream of input data, the control unit determines the current absorbed by the electric motor, and controls the motor so that the file alternates the direction of rotation at a frequency of from 1 to 20 Hz between a first direction and a second direction opposite to the first direction, and whereby the control unit controls the electric motor so that the file continuously rotates in the second direction when the monitored data fulfils a predetermined torque threshold condition during rotation in the first direction.

15 Claims, 7 Drawing Sheets

(56) References Cited

U.S. PATENT DOCUMENTS 6,293,795 B1 * 9/2001 Johnson ............... A61C 1/0015
433/102
6,591,698 B1 * 7/2003 Carlsson ............ A61B 17/1626
73/862.18

* cited by examiner

DENTAL HANDPIECE

This is a national stage application of PCT/EP2012/003725, filed Sep. 5, 2012, which claims priority to EP11007352.5, filed Sep. 9, 2011.

FIELD OF THE INVENTION

The present invention relates to a dental handpiece for the endodontic treatment of a root canal. The present invention also relates to a kit-of-parts comprising the dental handpiece and an endodontic file. Finally, the present invention relates to a process for controlling the electric motor of a dental handpiece.

BACKGROUND OF THE INVENTION

The endodontic treatment of a root canal includes the preparation of the root canal by extracting any soft dental tissue and shaping of the root canal followed by the obturating of the root canal with a suitable filling material. Typically, a procedure consists of opening the crown with a series of burs and diamond cutting instruments. Once the crown has been accessed, the pulp is removed with endodontic instruments, leaving the root canal space empty. This space is then disinfected. Subsequently, the canal space is filled with an inert material such as gutta percha and then the crown of the tooth is restored which may involve replacing the natural crown with a crown made of metal or porcelain.

Due to the small dimensions of the root canal, endodontic instruments, such as files and reamers, generally need to be small in size and made of hard materials to cut the dentin. In view of these constraints and the limited elasticity of the material of the endodontic instrument, a risk of the failure of the endodontic instrument exists during the treatment.

The preparation of the root canal by using rotary endodontic files driven by dental handpieces is known. Dental handpieces are able to apply a high torque to the endodontic file which is sufficient to break the endodontic file in the root canal. In this catastrophic case, a portion of the endodontic file remains in the root canal. As a consequence, time consuming and additional treatment steps are required which are uncomfortable for the patient, or the tooth to be treated may even have to be extracted.

From the prior art, a number of measures are known for avoiding that a rotary endodontic file breaks off in the root canal during the procedure.

In general, such measures lead to a complication of the preparation of the root canal and thereby cannot be considered to be desirable in the context of endodontic treatment.

Specifically, endodontic file systems including a set of files are used in sequence, for example in the "crown down" technique or "step back" technique. In the "crown down" technique, instruments with larger tapers are followed by instruments with smaller tapers in order to cut dentine from the crown to the apex and not along either the full inner surface length of the root canal or along the length of the file surface.

Accordingly, by using rotary endodontic files, it is impossible to prepare the entire root canal with a single rotary endodontic file without accepting a high risk that the file breaks off in the root canal during the procedure.

As an alternative to the endodontic treatment of a root canal by using rotary endodontic files, dental handpieces were suggested which alternate the direction of rotation of the rotary endodontic file at a frequency of from 1 to 20 Hz between a first direction and a second direction opposite to the first direction (reciprocating). The first direction may be the cutting direction of the endodontic file wherein the arc of rotation is larger than the arc of rotation in the second direction which is opposite to the first direction.

Given that the endodontic file changes the direction of rotation periodically, the risk of the file breaking off in the root canal is reduced provided the dental handpiece does not exert a torque in the order of the elastic limit of the endodontic file while the endodontic file is immobilized in the root canal.

However, even if the endodontic file gets immobilized in the root canal during rotation in a first direction which is usually a cutting direction, it is possible that the subsequent rotation in the opposite direction liberates the file so that the preparation of the root canal in endodontic treatment is not interrupted.

EP 10 013 364.4 of the present applicant discloses a dental handpiece which allows the preparation of a root canal by using a single file in a reciprocating mode.

However, since root canal instruments operated in the reciprocating mode cut on their full length or at least on more blades or surface area than if operated in continuous rotary mode or in the endodontic "crown down" or "step back" technique, a higher torque load especially in long narrow root canals must be applied when using reciprocating endodontic files.

Accordingly, in case of a reciprocating rotation of the endodontic file, it is possible that the endodontic file gets stuck in the root canal for the following reason:

In practice, a dental handpiece provides a maximum torque of a given magnitude due to the constraints on the dental handpiece regarding acceptable size and weight. In case the maximum torque is applied to the endodontic file in the first direction being the cutting direction, the endodontic file will be worked into the wall of the root canal with maximum torque and then stops. Since the sliding friction coefficient $\mu_s$ is smaller than the kinetic friction $\mu_k$ coefficient, the maximum torque of the handpiece might not be sufficient to liberate the endodontic file when the direction of rotation is changed. Accordingly, despite the reciprocating rotation of the endodontic file, the endodontic file may get immobilized in the root canal.

In order to address this problem, it was suggested to limit the torque applied to the endodontic instrument. For this purpose, it was suggested that a torque threshold should be introduced which limits the torque applied to the endodontic instrument. However, torque control with a reciprocating endodontic file is a complex problem. Different from the situation with a rotary endodontic file driven in continuous rotary mode, the torque applied to the endodontic file operated in reciprocating mode is not proportional to the current absorbed by the electric motor throughout the entire sequence of rotation. The time dependent alternation of the direction of rotation gives rise to time dependent effects on the current absorbed by the electric motor. For example, effects due to the acceleration and deceleration of the endodontic file, limited possibilities of averaging over a time interval, reaction times during the measurement, or effects due to the reversal of magnetisation provide erroneous data which cannot be used for deriving a realistic torque indicative of the state of the endodontic file.

US2002/0064756 discloses a dental handpiece for forming root canals comprising a motor, a cutting tool driven by said motor, and control means for automatically and periodically reversing the motor according to preset rotation periods of the tool in one direction and in the opposite one, respectively. Means for detecting the load torque applied to the tool may also be enabled during continuous rotation, so that the control means reverse the motor when the torque detected by the load torque detection means reaches a preset reference value during continuous rotation.

According to US2002/0064756, besides providing the reversal of motor when the load torque applied to the tool has reached a preset reference torque, the handpiece may use a different control procedure, not making use of the detection of the load torque applied to the tool. In such procedure, after disabling the torque detection means, motor and consequently tool operate in a reciprocating manner, with preset rotation periods TF and TR in the two directions, respectively. Accordingly, US200210064756 does not disclose a method wherein torque control is carried out during reciprocating of the tool. US200210064756 states specifically that during the F+R control, neither the load torque nor the speed are detected. US2002/0064756 recognizes that as to the speed, the motor is reversed at a very fast pace, and therefore is always in a transient state, with operating features which are very far from the standard ones and thus are not considered to be significant. Besides, in the F+R operation, tool is considered not to be subject to any torsion because it is assumed that the reversal of the motion occurs well before that the same tool may be jammed in the dental root canal.

However, the assumptions made according to US2002/0064756 are not correct since despite the reciprocating movement the failure of the tool occurs according to US2002/0064756.

SUMMARY OF THE INVENTION

It is therefore the problem of the present invention to provide a dental handpiece for the endodontic treatment of a root canal which may be used for preparing a root canal by using a single reciprocating endodontic file while at the same time the dental handpiece may be compact and lightweight and minimizes the risk of the endodontic file getting stuck or breaking off in the root canal.

Moreover, it is a further problem of the present invention to provide a kit-of-parts including the dental handpiece and an appropriate reciprocating endodontic file.

Finally, it is a problem of the present invention to provide a process for controlling a dental handpiece so that the risk of the reciprocating endodontic file getting stuck in the root canal is minimized while at the same time the dental handpiece may be lightweight and compact.

This problem is solved according to the invention according to the claims. The present invention provides a dental handpiece for the endodontic treatment of a root canal, comprising
(i) a chuck for attaching and holding an endodontic file;
(ii) an electric motor having a shaft for driving the endodontic file;
(iii) a control unit for controlling the motor, which receives a stream of input data; characterized in that while monitoring the stream of input data, the control unit determines the current absorbed by the electric motor, and controls the motor so that the file alternates the direction of rotation at a frequency of from 1 to 20 Hz between a first direction and a second direction opposite to the first direction, and whereby the control unit controls the electric motor so that the file continuously rotates in the second direction when the monitored data fulfils a predetermined torque threshold condition during rotation in the first direction.

Moreover, the present invention provides a kit-of-parts comprising the dental handpiece for the endodontic treatment of a root canal and an endodontic file.

Finally, the present invention provides a process for controlling the electric motor of a dental handpiece said process being characterized by
(i) providing a dental handpiece according to the invention,
(ii) monitoring the input data by a control unit;
(iii) controlling the motor so that the file alternates the direction of rotation at a frequency of from 1 to 20 Hz between a first direction and a second direction;
(iv) controlling the motor so that the file continuously rotates in the second direction when the monitored data fulfil a predetermined torque threshold condition during rotation in the first direction.

The present invention is based on the recognition that torque control in the direction of rotation opposite to the first direction is not necessary and may even be detrimental to the success of the endodontic treatment. Rather, in view of the differences between the sliding friction and the kinetic friction, it is acceptable to apply the maximum torque of the handpiece in the second direction of rotation opposite to the first direction, provided that the torque applied to the reciprocating endodontic file during rotation in the first direction is limited by a specific torque threshold which should be at most in the order of the maximum torque provided by the dental handpiece corrected by the ratio of the sliding friction coefficient $\mu_s$ and the kinetic friction $\mu_k$ coefficient and less than the elastic limit of the endodontic file.

Accordingly, the present invention is based on the concept that the catastrophic failure of the endodontic file may be avoided when selectively applying a torque threshold in the first direction and monitoring the preparation of the root canal for the attainment of this torque threshold during rotation in the first direction, followed by a rotation of the endodontic instrument in the second direction without applying a torque threshold or by increasing the torque threshold so as to remove the file from the root canal for cleaning.

According to the present invention, torque control adapts the limited resources of a compact and lightweight dental handpiece to a reciprocating endodontic treatment wherein the catastrophic failure of the endodontic file is avoided due to the specific reciprocating rotary movement and since the torque control always provides additional torque in the direction of rotation opposite to the cutting direction so that the endodontic file may be liberated efficiently when temporarily stuck in the root canal.

The present invention also provides the following additional benefits:

Since the torque increases also when the flutes of the file are filled with debris, the probability of reaching torque threshold condition increases when the flutes are filled. Accordingly, less debris remains in the flutes and thus less potentially infected debris pressed within dentin tubules. The feedback indicates increased stress on the dental handpiece of the invention and a need to brush canal walls in order to create more space, thus reducing stress on the dental handpiece.

The practitioner receives feedback about the wrong application of the file and that he should clean file's flutes and brush the root canal. This helps clinician to use file correctly/avoid misuse of the file.

Mechanical parts e.g. contra angle and its gears, are protected and have a higher life span as a result.

Hand piece will be lighter in weight.

Power supply will be smaller, less expensive and of less weight.

DETAILED DESCRIPTION OF THE PREFERRED EMBODIMENTS

For the purpose of the present disclosure, the first direction of rotation may be the cutting direction of the reciprocating endodontic file, the direction in which the rotation continues longer than the rotation in the opposite direction or travels a greater angle. The second direction is the direction in which the endodontic file is liberated and/or removed out of the root canal.

Figure 1:
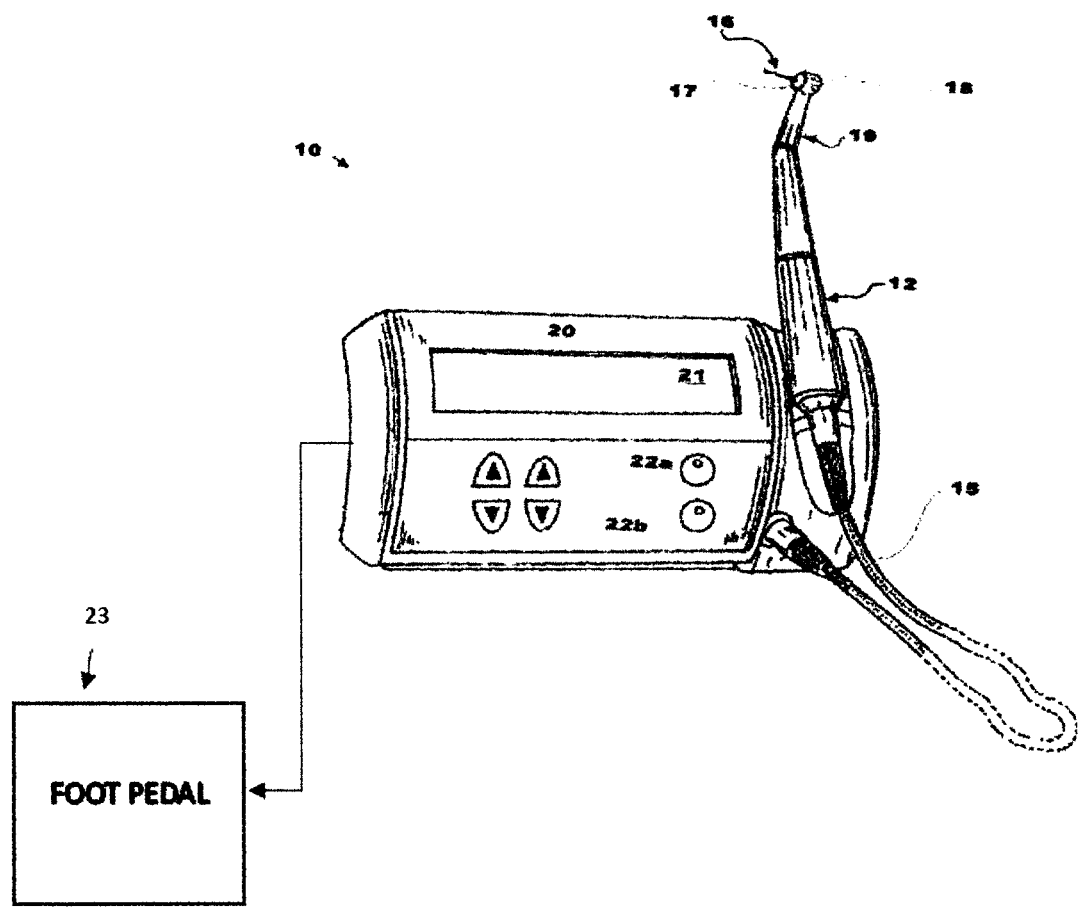
FIG. 1 shows a system for performing endodontic procedures

A dental handpiece for the endodontic treatment of a root canal according to the present invention comprises
(i) a chuck for attaching and holding an endodontic file;
(ii) an electric motor having a shaft for driving the endodontic file;
(iii) a control unit for controlling the motor, which receives a stream of input data;

As shown in FIG. 1, a dental handpiece 10 includes a control unit 20. An endodontic instrument or file 16 is held securely in a chuck 17 of a handpiece head 18 for rotation about its longitudinal axis. File 16 may be any endodontic instrument of useful design. Head 18 is an integral component of a conventional contra angle 19, providing a drive train and gears necessary to rotate file 16. An electric motor 12 is fastened to contra angle 19, usually by way of complementary threaded body parts, and engages the drive train of contra angle 19 to rotate file 16. Electric motor 12 is connected by a control cable 15 to control unit 20, which typically includes a microprocessor unit. Control unit 20 is capable of electronically controlling and programming motor parameters such as speed, torque, and direction of rotation for a selected endodontic type file.

Control unit 20 includes software providing means for setting the regime or method of rotation of the endodontic file 16. Settings may preferably appear in a display 21. In addition, microprocessor may preferably provide keys (22a, 22b) allowing setting of the time between the forward and reverse motions. In addition, the microprocessor may be connected to a user interface providing keys allowing changing, disabling and enabling the settings.

According to a preferred embodiment, the control unit is connected to a foot pedal 23 or manual switch (FIG. 2) for stopping the continuous rotation and/or alternating rotation of the endodontic file.

An endodontic file 16 is preferably configured including an elongated tapered metal file portion having a proximal end, a distal end, and at least three spaced apart helical flutes with spiralled lands therebetween. Distal end is dimensioned and configured for a selected finished root canal apex and tapered portion is configured to provide a desired finished root canal configuration.

The present invention also provides a kit-of-parts comprising the dental handpiece according to the invention, and an endodontic file.

Figure 2:
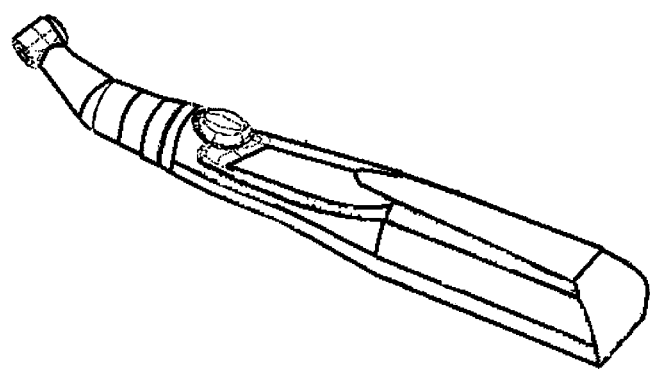
FIG. 2 shows an elevated view of a cordless handpiece.

As shown in FIG. 2, the dental handpiece may be cordless. Accordingly, the control unit may be incorporated inside the dental handpiece. Alternatively, the control unit may be connected to the dental handpiece by a wireless connection. In case the control unit is connected to the dental handpiece by a wireless connection, the control unit may be provided with a foot pedal 23 as in the case of the dental handpiece shown in FIG. 1.

According to a preferred embodiment, the electric motor is a brushless electric motor. Preferably, the electric motor is powered by direct-current (DC) electricity and has electronic commutation systems. According to a preferred embodiment, the current-to-torque and frequency-to-speed relationships are linear during continuous rotary operation. In particular, the electric motor may be a stepper motor. A brushless electric motor according to a preferred embodiment of the present invention offers advantages over brushed DC motors, including more torque per weight, more torque per watt (increased efficiency), increased reliability, reduced noise, longer lifetime (no brush and commutator erosion), elimination of ionizing sparks from the commutator, and overall reduction of electromagnetic interference (EMI).

According to a preferred embodiment, the rotation in the first direction and in the second direction is determined by a plurality of hall sensors 24. Preferably, the hall sensors 24 provide a stream of input data to the control unit relating to the position of the shaft, direction of rotation, and/or speed of rotation in the first and second direction.

According to a further preferred embodiment, torque is determined by passing the current absorbed by the motor though a resistor and determining the drop voltage. Moreover, the control unit may use the current absorbed by the electric motor and one or more parameters of the endodontic file for determining the predetermined torque threshold condition. The parameters of the endodontic file may be entered or modified by the user or may be retrieved from a storage medium.

Figure 3:
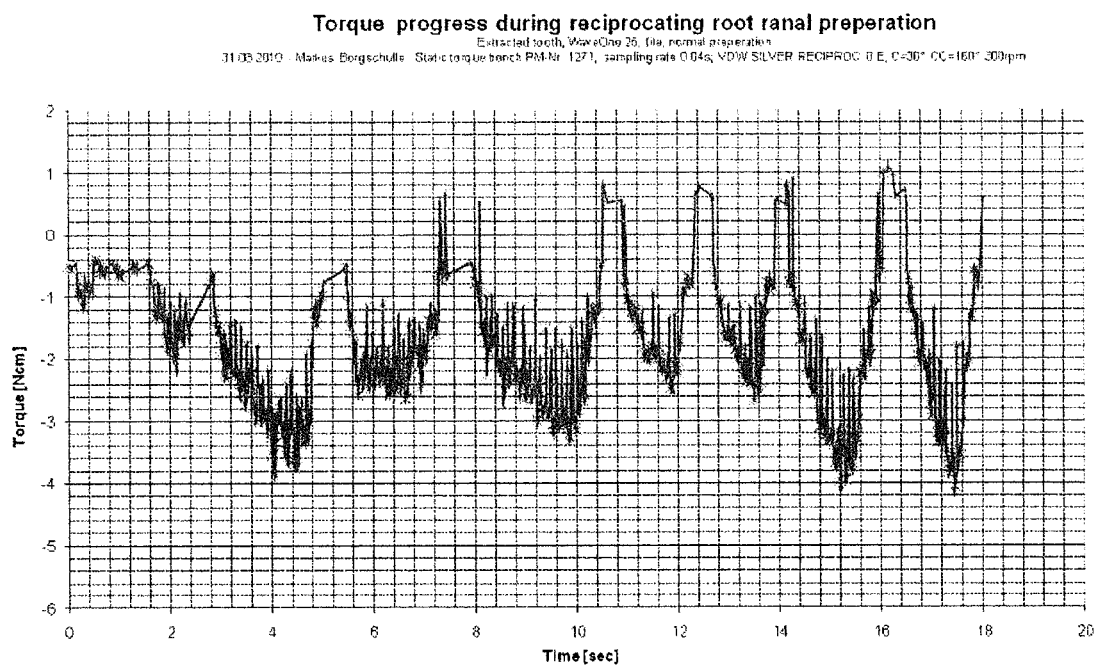
FIG. 3 shows raw measured during reciprocating endodontic treatment from which information on torque applied to the endodontic file may be derived.

FIG. 3 shows data relating to the torque applied to the endodontic file during reciprocating root canal preparation. Negative torque values represent torque during rotation in the first direction. Positive torque values represent torque during rotation in the second direction. The torque varies from about −4 Ncm tool about +1 Ncm in this example.

The dental handpiece for the endodontic treatment of a root canal according to the present invention is characterized in that while monitoring the stream of input data, the control unit determines the current absorbed by the electric motor, and controls the motor so that the file alternates the direction of rotation at a frequency of from 1 to 20 Hz between a first direction and a second direction opposite to the first direction.

The preferred regime of operation during alternating rotation is that the rotation in the first direction exceeds that of the rotation in the second direction opposite to the first direction such that file 16 rotates through a series of motions in first and second directions and completes a circle of rotation such that cleaning of the root canal proceeds by means of a series of cycles. The rotation in the first direction is preferably a rotation in the range of from 45 to 360°, more preferably from 60 to 270°. The rotation in the second direction is preferably a rotation of a smaller angle as the rotation in the first direction and is controlled to be in the range of from 30 to 270°, preferable 45 to 180°.

The dental handpiece for the endodontic treatment of a root canal according to the present invention is further characterized in that the control unit controls the electric motor so that the file continuously rotates in the second direction when the monitored data fulfils a predetermined torque threshold condition during rotation in the first direction.

Figure 4:
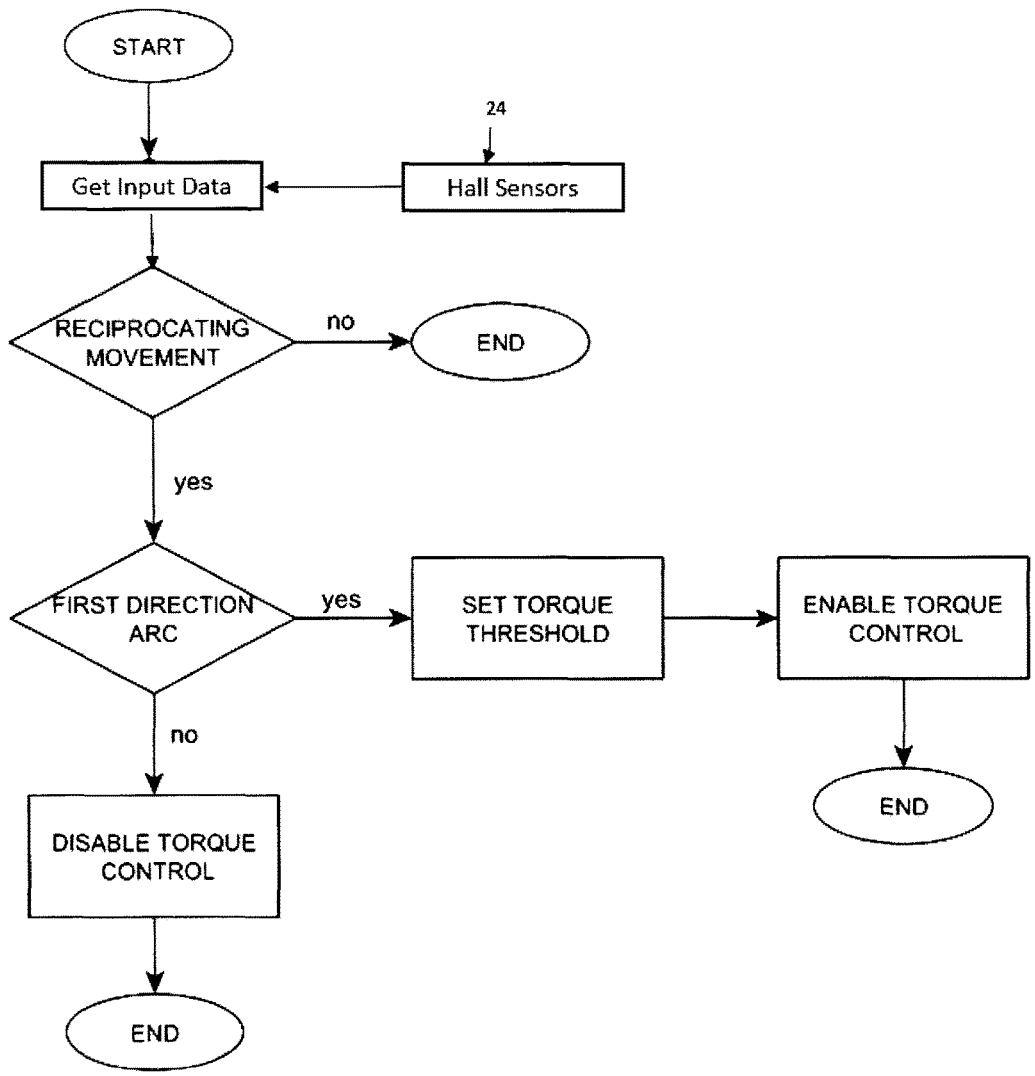
FIG. 4 is a block diagram of an example endodontic procedure using the handpiece of the present invention.

FIG. 4 shows a block diagram of software by which the control unit controls the electric motor. Accordingly, when the software is initialized, the software determines as to whether the endodontic file is driven in a reciprocating movement. In the affirmative, the software determines as to whether the arc of rotation is in the second direction. In the affirmative, the software disables the torque control and terminates the cycle. However, if the software determines that the rotation is in the first direction, a torque threshold is applied. The software may determine the torque threshold based on a constant value programmed into the software. Alternatively, the software may retrieve a value for the torque threshold from a memory location which is either changed by the input of the user or which forms part of a database or which is determined by the position of the endodontic file I the root canal. Optionally, the software may adapt the value for the torque threshold by taking further parameters into account. Once the torque threshold has been set, torque control is enabled and the software terminates the cycle. Subsequent to the termination of the cycle, the software may start over with checking as to whether the movement of the file is reciprocating.

Preferably, the software derives the value for the torque threshold from a table and adapts the torque threshold value based on additional parameters such as the type of the endodontic file, the service life of the specific endodontic file, and optionally additional input provided by the user.

Figure 5:
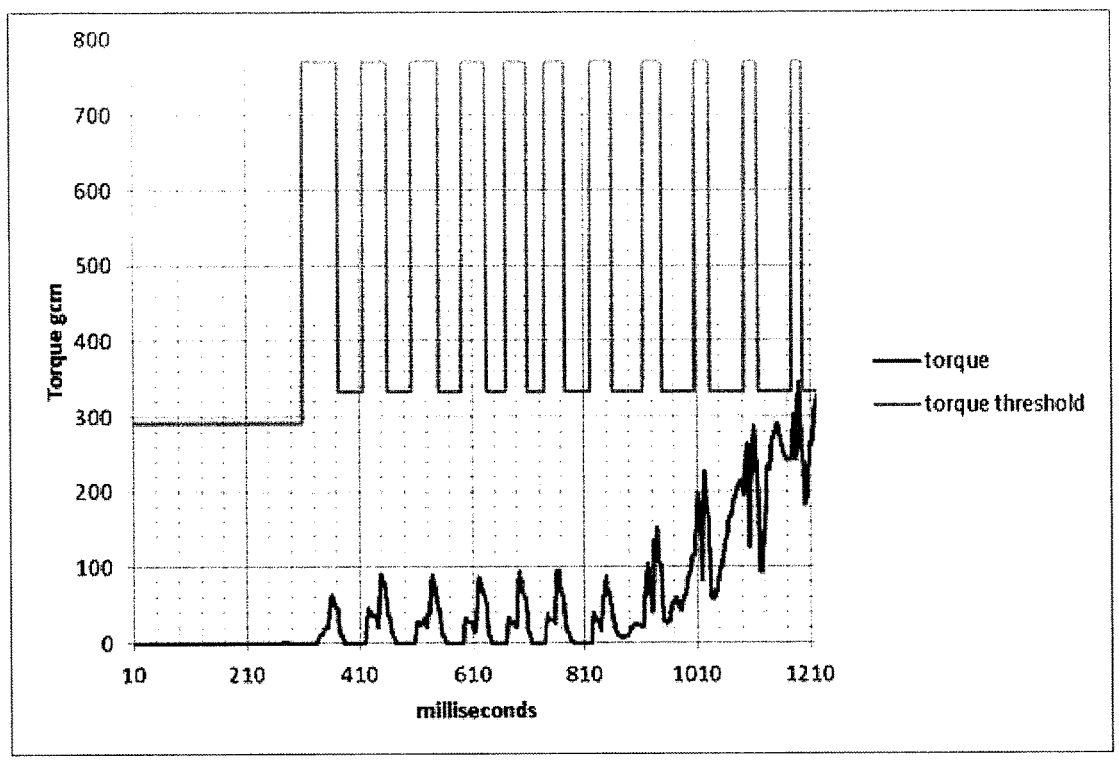
FIG. 5 shows the curve of the input data stream received by the control unit relating to the current consumed by the electric motor as a function of time and the curve of the torque threshold set by the software during the reciprocating movement.

As shown by FIG. 5, the reading of the current consumed by the electric motor shows peaks every time the motor inverts the directional status due to the current needed to perform the inversion. Such peaks cannot be considered as valid torque readings. The peaks are ignored by setting the torque threshold to a maximum during the rotation in the second direction. During rotation in the first direction, the threshold is applied at the desired level. When the reading of the input data stream received by the control unit which corresponds to the torque applied to the endodontic file in the first direction reaches a predetermined value, the control unit controls the electric motor so that the file continuously rotates in the second direction.

Figure 6:
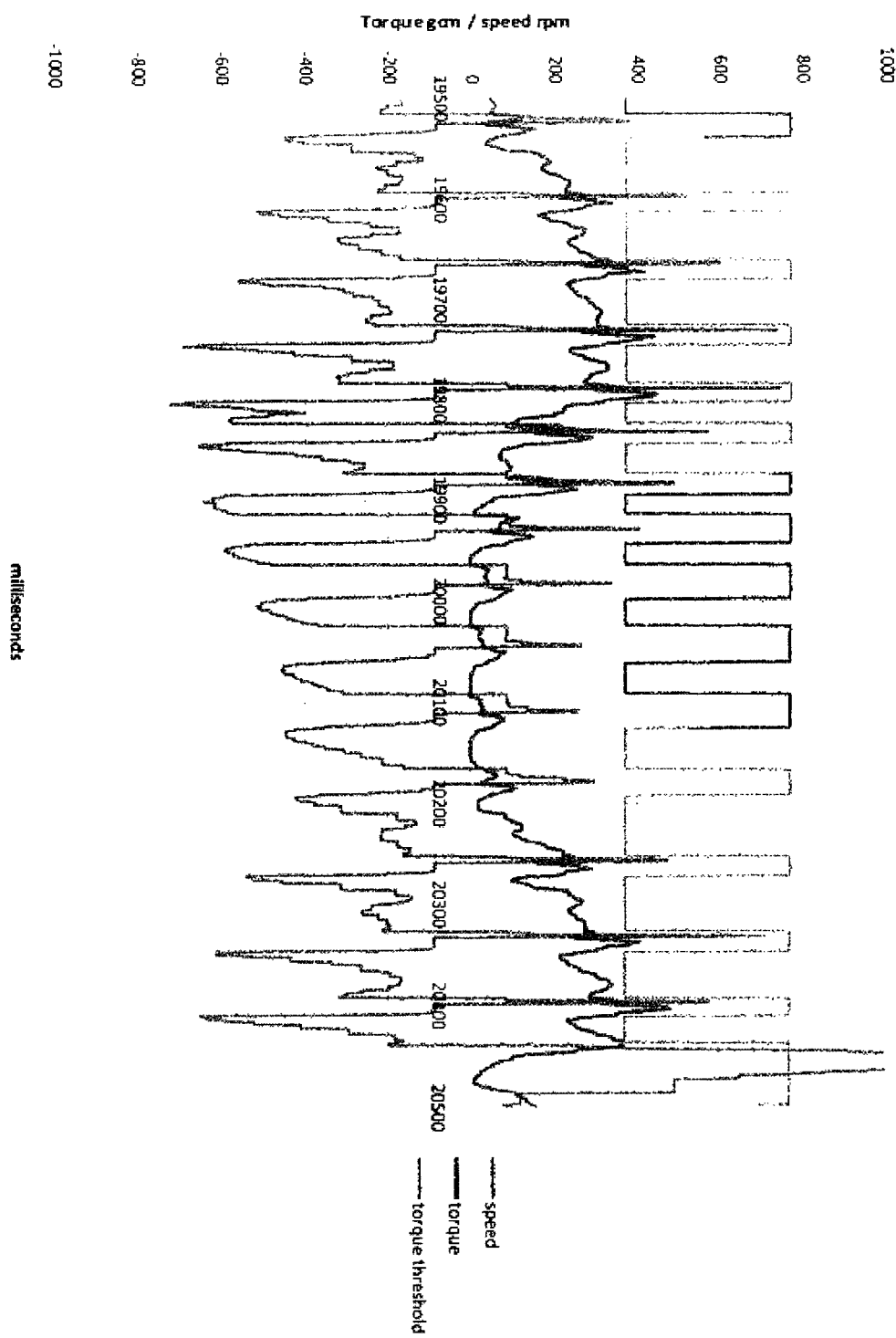
FIG. 6 shows a curve of the speed of the tool and the torque applied to the tool as well as the torque threshold set by the software during the reciprocating movement.
Figure 7:
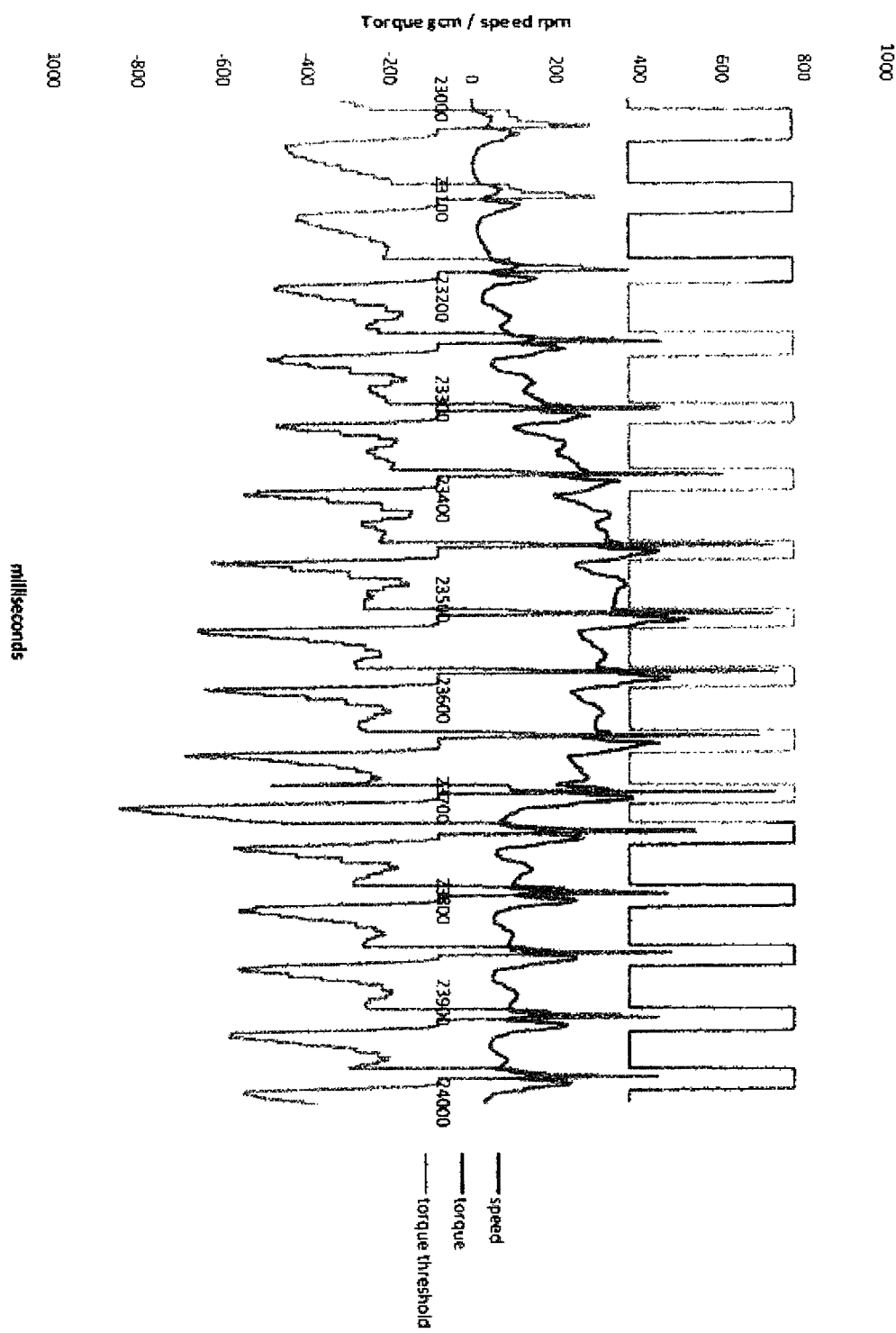
FIG. 7 shows a further curve of the speed of the tool and the torque applied to the tool as well as the torque threshold set by the software during the reciprocating movement.

As shown by FIGS. 6 and 7, the observed torque maximum derived from the input data stream during rotation in the first direction is significantly lower than the observed torque maximum derived from the input data stream during rotation in the second direction. Also, the observed maximum speed of rotation derived from the input data stream during rotation in the first direction is significantly lower than the observed maximum speed of rotation derived from the input data stream during rotation in the second direction. The differences are due partly to measurement artifacts. In case such measurement artifacts would be made the basis of the control of the reciprocating movement, the efficiency of the endodontic treatment could not be optimized since the torque threshold would prematurely terminate the reciprocating movement based on the input data stream received during rotation in the second direction. Therefore, it is essential according to the present invention to be able to determine with certainty the state of the tool with regard to the rotational direction, which is not possible by using a MOSFET bridge comprising upper legs, controlled by PWM signals for the reciprocating operation of the motor, and lower legs, earthed via a low-value resistor from which a feedback signal for the load torque detection means is obtained as disclosed by US2002/0064756.

According to the present invention, the torque applied in the reciprocating mode is measured and controlled in such a way that the torque applied will not exceed a first threshold (T) determined by the following formula:

$$T = T_{max}\, \mu_s/\mu_k$$

wherein $T_{max}$ is the maximum possible torque level of the handpiece or the clinical torque maximum, whatever is lower, $\mu_s/\mu_k$ is the ratio of the sliding torque coefficient and the kinetic torque coefficient. Specifically, the predetermined torque threshold condition includes a maximum torque in the range of from 0.5 to 15 Ncm. More preferably, the predetermined torque threshold condition includes a maximum torque in the range of from 2 to 10 Ncm, still more preferably the predetermined torque threshold condition includes a maximum torque in the range of from 3 to 6 Ncm. Accordingly, the electric motor has sufficient torque for liberating a file which is temporarily stuck in the root canal despite the fact that the sliding friction coefficient $\mu_s$ is smaller then that kinetic friction $\mu_k$.

Preferably, the control unit triggers a user feedback as visual and/or acoustic warning and/or vibration of the handpiece by the change of rotation when the monitored data fulfils a predetermined torque threshold warning condition during rotation in the first direction. Alternatively or additionally, the user may prevent the control unit from controlling the electric motor based on a predetermined torque threshold condition during rotation in the first direction. Alternatively or additionally, the control unit may monitor the location of the file tip in the root canal. Moreover, any function may be disabled or the torque threshold increased or decreased by the user.

After the control unit has controlled the electric motor to continuously rotate the file in the second direction so that the file is liberated and debris is removed from the root canal, the control unit may continue according to different alternatives:

a. A defined torque threshold is exceeded
 i. Then stop (re-start by releasing and pressing the foot pedal)
 ii. And/or then automatically re-start in reciprocating mode
b. A defined angle of rotation or rotation time is exceeded
 i. Then stop (re-start by releasing and pressing the foot pedal)
 ii. And/or then automatically re-start in reciprocating mode The present invention also provides a process for controlling the eclectic motor of the dental handpiece of the present invention, said process being characterized by
 (i) providing the dental handpiece
 (ii) monitoring the input data by a control unit;

(iii) controlling the motor so that the file alternates the direction of rotation at a frequency of from 1 to 20 Hz between a first direction and a second direction;
(iv) controlling the motor so that the file continuously rotates in the second direction when the monitored data fulfil a predetermined torque threshold condition during rotation in the first direction.

The invention claimed is:

1. A dental handpiece for an endodontic treatment of a root canal, comprising:
   (i) a chuck for attaching and holding an endodontic file;
   (ii) an electric motor having a shaft for driving the endodontic file;
   (iii) a control unit for controlling the electric motor in a rotary mode and a reciprocating mode, which monitors a stream of input data;
   wherein while monitoring the stream of input data, the control unit determines a current absorbed by the electric motor, and controls the electric motor in the reciprocating mode wherein the endodontic file alternates the direction of rotation at a frequency of from 1 to 20 Hz between a first direction and a second direction opposite to the first direction,
   wherein when a monitored data fulfils a predetermined torque threshold condition during rotation in the first direction while in the reciprocating mode, the reciprocating mode terminates and the rotary mode initiates wherein the endodontic file continuously rotates in the second direction to liberate the endodontic file from the root canal despite a sliding friction coefficient μs being smaller than a kinetic friction coefficient μk; and
   wherein a torque applied in said reciprocating mode does not exceed said predetermined torque threshold and wherein said predetermined torque threshold is configured to be at most in an order of the maximum torque provided by the dental handpiece multiplied by a ratio of the sliding friction coefficient μs and the kinetic friction μk coefficient and less than an elastic limit of the endodontic file.

2. The dental handpiece according to claim 1, wherein the control unit is connected to a foot pedal for stopping the continuous rotation and/or alternating rotation of the endodontic file.

3. The dental handpiece according to claim 1, wherein the electric motor is a brushless electric motor.

4. The dental handpiece according to claim 1, wherein a plurality of hall sensors provide the stream of input data to the control unit, which determines the rotation in the first direction.

5. The dental handpiece according to claim 4, wherein the hall sensors provide the stream of input data to the control unit relating to the position of the shaft, direction of rotation, and/or speed of rotation in the first and second direction.

6. The dental handpiece according to claim 1, wherein the predetermined torque threshold condition is determined by passing the current absorbed by the electric motor though a resistor and determining a drop voltage.

7. The dental handpiece according to claim 1, wherein the control unit uses the current absorbed by the electric motor and one or more parameters of the endodontic file for determining the predetermined torque threshold condition, the one or more parameters being selected from the group consisting of the type of the endodontic file and the service life of the specific endodontic file.

8. The dental handpiece according to claim 7, wherein the parameters of the endodontic file are entered or modified by the user or are retrieved from a storage medium.

9. The dental handpiece according to claim 1, wherein the control unit triggers an acoustic warning sound when the monitored data fulfils the predetermined torque threshold condition during rotation in the first direction.

10. The dental handpiece according to claim 1, wherein the control unit monitors a location of the endodontic file tip in the root canal.

11. The dental handpiece according to claim 1, wherein the user may prevent the control unit to control the electric motor based on the predetermined torque threshold condition during rotation in the first direction.

12. The dental handpiece according to claim 1, wherein the predetermined torque threshold condition includes a maximum torque in the range of from 0.5 to 15 Ncm.

13. A kit-of-parts comprising the dental handpiece according to claim 1 and an endodontic file.

14. The kit-of-parts according to claim 13, wherein the first direction is a cutting direction of the endodontic file.

15. A process for controlling the electric motor of the dental handpiece as defined by claim 1, said process being characterized by
   (i) providing the dental handpiece as defined by claim 1,
   (ii) monitoring the input data by the control unit;
   (iii) controlling the electric motor so that the endodontic file alternates the direction of rotation at the frequency of from 1 to 20 Hz between the first direction and the second direction;
   (iv) controlling the electric motor so that the endodontic file continuously rotates in the second direction to liberate the endodontic file from the root canal when the monitored data fulfils the predetermined torque threshold condition during rotation in the first direction.

* * * * *